United States Patent [19]

Johnston

[11] 4,173,217
[45] Nov. 6, 1979

[54] MASSAGE APPARATUS

[76] Inventor: Lyman C. Johnston, 12 Boulton Dr., Toronto, Ontario, Canada

[21] Appl. No.: 744,385

[22] Filed: Nov. 23, 1976

[30] Foreign Application Priority Data

Jul. 18, 1976 [CA] Canada ................................ 256590

[51] Int. Cl.² .......................................... A61H 29/00
[52] U.S. Cl. .................................. 128/734; 128/24.5
[58] Field of Search ....................... 128/24.4, 24.5, 25, 128/51, 52, 2.1 Z

[56] References Cited

U.S. PATENT DOCUMENTS

| | | | |
|---|---|---|---|
| 2,184,511 | 12/1939 | Bagno et al. | 128/2.1 Z |
| 2,964,037 | 12/1960 | Johnston | 128/49 |
| 3,094,119 | 6/1963 | Avedissian | 128/49 |
| 3,546,064 | 10/1970 | Kuroda et al. | 128/49 |
| 3,870,034 | 3/1975 | James | 128/2.1 Z |
| 3,901,214 | 8/1975 | Taaffe | 128/2.1 Z |
| 3,980,077 | 9/1976 | Shaw | 128/2.1 Z |

*Primary Examiner*—Lawrence W. Trapp
*Attorney, Agent, or Firm*—William T. Howell

[57] ABSTRACT

Massage apparatus for treatment of deep muscle in body tissue has a galvanic skin reactor having electrodes adapted to be attached to the skin combined with a massage device having massage elements with an amplitude of between ½ to 1" operating at a frequency of about 22 cycles per second, said galvanic reactor having response mechanism to indicate the change in resistance between the electrodes and enclosed skin caused by application of the massage elements.

1 Claim, 5 Drawing Figures

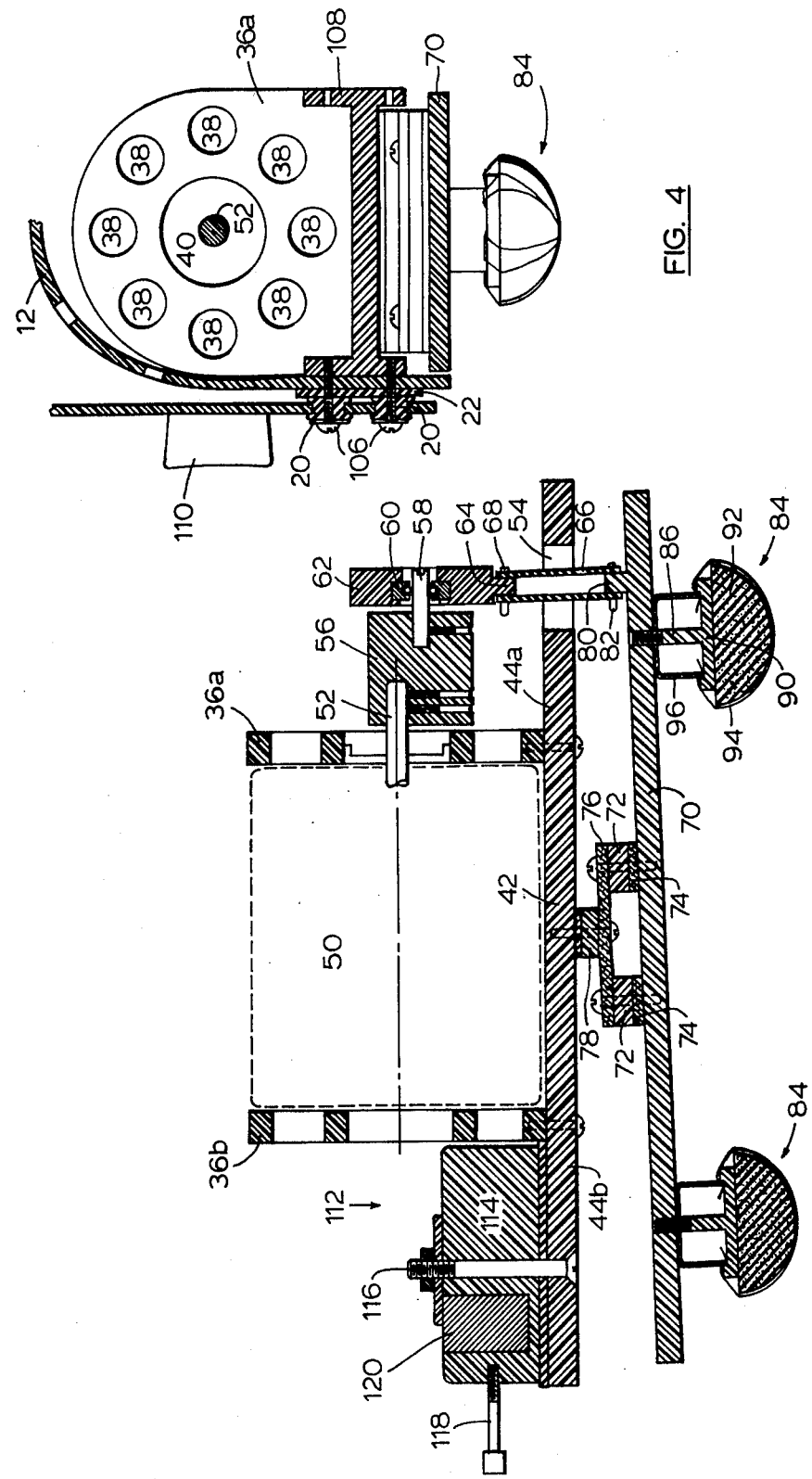

MASSAGE APPARATUS

FIELD OF THE INVENTION

This invention relates to the therapeutic treatment of body tissue by massage.

PRIOR ART

Many devices have been developed as a substitute for the use of hands in massaging body tissue, but such device is described in U.S. Pat. No. 2,964,037 which comprises a rocking member, drive means, an elastomeric pivot, a drive connecting member and massage elements which are adjustable in position with respect to the pivot to vary their amplitude.

A problem in such devices is to provide sufficient amplitude to the massage elements which effect deep muscle penetration and yet permit the operator to hold the device without discomfort. In known devices, the greater the amplitude, the greater the vibrations transmitted to the hands of the holder, thus rendering them insensitive.

An improvement in the device described in the above mentioned U.S. Pat. No. 2,964,037 is disclosed in my co-pending U.S. patent application number 744,383 filed Nov. 23, 1976, now abandoned. A feature of the device is that reciprocating massage elements therein may have an amplitude of between ½ to 1" at a frequency of about 22 cycles per second while the operator is able to hold the device with practically no vibration transmitted to the hands. Furthermore, the weight alone of the device, when placed on body tissue is sufficient to provide the above frequency at the specified range of amplitude with the result that the operator can effect the same deep muscle treatment at repeated intervals.

However, the location of the muscular portion of the body tissue in need of treatment is dependent on the skill of the operator and whose judgement alone determines the effect of the massage treatment.

SUMMARY OF THE INVENTION

It is an object of the invention to provide a method and apparatus which minimizes the skill of the operator in locating and treating deep body muscle by massage while also assessing the subsequent effect thereof.

The invention in its broadest sense involves the steps of attaching to the skin of the person being treated, the electrodes of a galvanic skin reactor, then applying to the body tissue reciprocating massage elements intended to cause muscular stretch reflex to affected muscles, which reflex will cause a change in resistance between electrodes and the underlying skin and measuring the change in resistance through the galvanic skin reactor.

More particularly, the invention involves the application of massage elements having an amplitude of between ½ to 1" operating at a frequency of about 22 cycles per second.

In greater particularity the invention involves the use of a massage device, the weight of which alone provides the frequency of about 22 cycles per second of the massage elements with an amplitude of between ½ to 1", such being particularly effective to deep muscle massage. With such a massage device the treatment can be repeated using the same pressure with the result that a valid comparison can be made, through the response of the galvanic skin reactor, of the extent of the stretch reflex of the muscles under treatment.

BRIEF DESCRIPTION OF THE DRAWINGS

The invention will now be described in relation to the accompanying drawings, in which:

FIG. 4 is a sectional view of the device shown in FIG. 2;

FIG. 5 is a cross sectional view taken on the lines 4—4 of FIG. 2.

DESCRIPTION OF A PREFERRED EMBODIMENT

In the description like numbers represent like parts.

Figure 1:
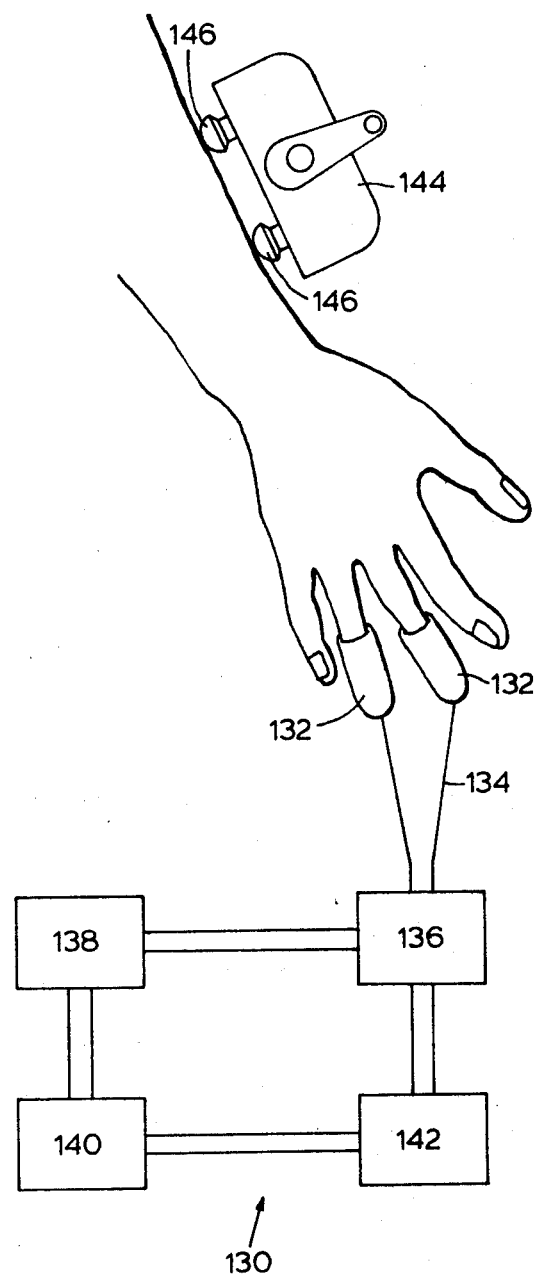
FIG. 1 is a diagrammatic representation of apparatus constructed according to the invention.

With reference to FIG. 1, the apparatus includes a galvanic skin reactor, generally denoted by the numeral 130, which has a pair of electrodes 132; each electrode is adapted to be attached to the skin of the person being treated and a particularly convenient form is illustrated in FIG. 1 in that each is shaped to fit over the end of a finger in thimble like manner.

The electrodes are connected through suitable leads 134 to an oscillator 136, amplifier 138, speaker 140 and meter 142, each depicted in box manner. The arrangement is such that any change in the resistance of the skin in contact with electrodes 132 caused by reaction of the body to external influences is measurable through the galvanic skin reactor, audibly through the speaker 140 and/or visually on the meter 142.

The apparatus also includes a massage device, shown in block form, generally indicated by the numeral 144, which has reciprocating massage elements 146 extending therefrom, each element having an amplitude of between ½ to 1" operating at a frequency of about 22 cycles per second, which range of amplitude and frequency is particularly beneficial for deep muscle massage.

The method of operation of the apparatus is to attach the electrodes 132 to the skin of the person being treated and then apply the massage elements 146 of the device 144 to the part of the body which appears to be in need of treatment. The particular muscles which will respond can be ascertained by the audio visual response denoted by the galvanic skin reactor when the elements are placed on the body tissue. More specifically, affected muscle responding to massage will undergo a higher stretch reflex than unaffected muscle and the natural body reaction to the higher stretch reflex will cause a change in resistance of the skin in contact with the electrodes 12. This change will be audibly indicated by an increase in the pitch of the speaker 140 and/or increase in the reading of the needle on the meter 142.

As the muscular stretch reflex diminishes due to the beneficial effect of the massage the stretch reflex of the affected muscles will also diminish and the pitch on the speaker will drop and/or the needle will show a lower reading.

It is common in massage treatment to temporarily discontinue in order to allow the muscles to relax and then follow with further treatment. The apparatus described above is particularly useful in determining the effect of the previous treatment when the massage is resumed because the visual response indicated on the meter 22 on resumption can be compared with the previous indicated response thus showing whether there has been an improvement in the muscular condition and the extent thereof. However, it will be appreciated that the comparison is valid only if the pressure, amplitude and frequency of the massage elements is practically the same in successive treatments.

To provide for these conditions the massage device 144, shown in outline in FIG. 1, is preferably constructed as illustrated in FIGS. 2, 3, 4 and 5, which device is described and claimed in my abandoned copending U.S. application Pat. No. 744,383.

Figure 2:
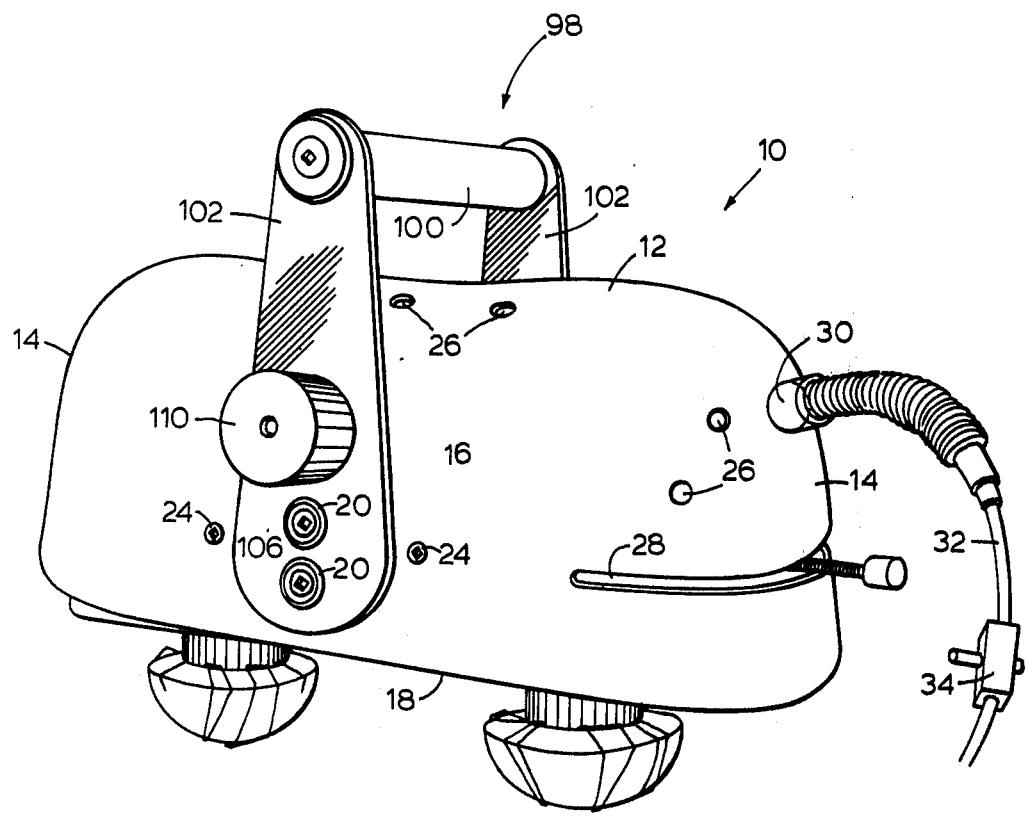
FIG. 2 is a view in perspective of a massage device preferably used in the apparatus depicted in FIG. 1.
Figure 3:
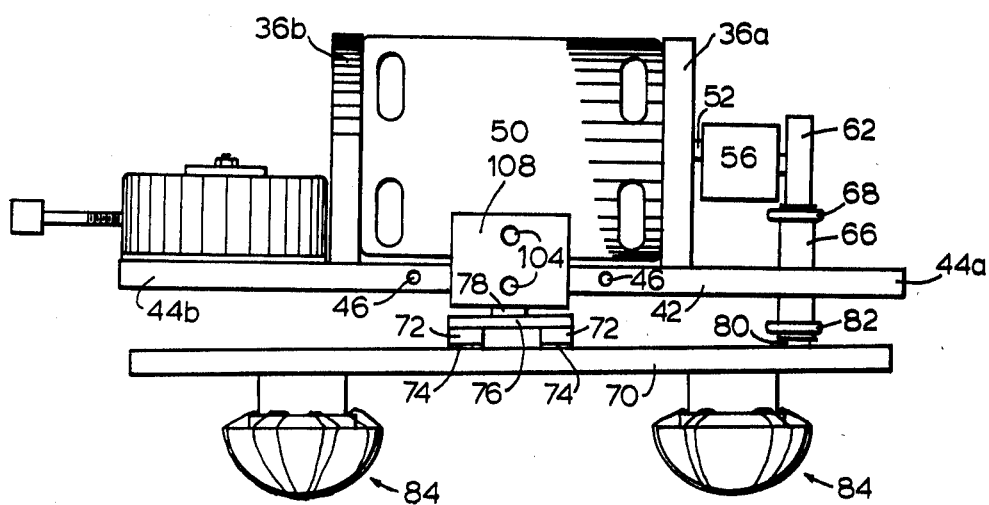
FIG. 3 is a side elevational view of the device shown in FIG. 2.

With reference to FIG. 2 the massage device has an elongated casing, generally denoted by the numeral 10 and preferably made of plastic. The casing 10 has a rounded top 12 which curves integrally into end walls 14 and substantially parallel side walls 16 to define an opening 18. Centrally located and traversing each side wall 16 are a pair of vertically disposed hollow rubber bushings 20 backed by a rubber pad 20, see FIG. 4. Each side wall 16 has a pair of apertures, which provide for securement by screws 24 of a rigid inner structure to be described later.

The casing 10 has a number of spaced apart apertures 26 located in the top 12 and the end walls 14; these apertures 26 provide for air circulation to connect heat away from the device when operating. A horizontally disposed slot 28 is located in one end wall 14 for a purpose to be described later. The casing 10 also has an opening 30 to permit entry of an electrical lead 32 which carries a conventional switch 34.

The rigid inner structure referred to above includes a pair of spaced apart vertically disposed plates 36a and 36b preferably made of plastic with each having a ring of apertures 38 which surround the central aperture 40. The plates 36a and 36b are secured normally to a horizontally disposed plate 42 short of the ends thereof, thus providing a pair of platforms 44a and 44b. The plate 42 is shaped to correspond with the opening 18, i.e. it has substantially parallel sides and rounded ends and the dimension of the plate 42 is such that it slides into the casing 10. The plate 42 has threaded holes 46 on its sides which provide for its securement to the casing 10 by means of the screws 24, The rigid structure formed of the plates 36a and 36b and 42 when secured in the casing 10 supports an electric motor, not shown in detail, generally denoted by the numeral 50 and having a protruding shaft 52. The motor 50 is secured to the plates 36a and 36b in such a manner that the shaft 52 extends through the central aperture 40 of the plate 26a. The ring of apertures 38 in each plate 36a and 36b provide for cooling.

Platform 44a of the plate 42 has a slot 54. The motor shaft 52 extends over the platform 44a to carry a circular sleeve 56 eccentrically secured thereto. A rod 58 centrally secured to the sleeve 56 extends over the slot 54. The rod 58 carries a bearing 60 which supports another sleeve 62 which has an integral stub arm 64 extending downwards towards the slot 54. A tubular flexible coupling 66 is secured to the stub arm 64 by means of a clip 68. The flexible coupling 66 extends through the slot 54.

Below the plate 42 and having a similar configuration is a rocker plate 70 which closes the opening 18 of the casing 10. The rocker plate 70 is mounted flexibly for pivotal movement on the transverse axis of the plate 42. The mounting comprises a pair of spaced apart transverse bars 72 secured to the top side of the rocker plate 70 each secured thereto through an intermediate fibre washer 74. The transverse bars 72 are joined at their upper surfaces by an elastomeric plate member 76. The lower side of the plate 42 has a centrally located transverse bar 78 which provides the pivotal axis for the rocker plate 70. The transverse bar 78 is secured on its underside to the mid portion of the elastomeric plate member 76, i.e. between the transverse bars 72.

The rocker plate 70 has an integral arm 80 on its upper side in line with the flexible coupling 66 and is secured thereto by a clip 82.

It will be apparent that when the motor 50 is switched on, the motor shaft 52, through the eccentrically located sleeve 56 and connected flexible coupling 66, will oscillate the rocker plate 70 about the transverse bar 78. Also the elastomeric plate member 76 provides for quiet operation.

A pair of massage elements each generally denoted by the numeral 84 extend from the underside of the rocker plate 70 outward of the casing 10. Each massage element 84 comprises a threaded rod 86 which may be located in a selected one of a series of correspondingly threaded holes in the rocker plate 70. This provides for adjustment of the position and thereby the stroke of the massage elements 86.

In the massage elements 84 shown, the threaded rod 86 terminates in a mushroom shaped cap 90 covered by a rubber pad 92. It is a feature of the massage elements 86 that for hygenic purposes they are designed so that the rubber pad 92 may be covered by a disposable plastic cover 94. This is accomplished by means of a cup like member 96, the base of which is centrally threaded to secure it to the threaded rod 86. The plastic cover 94 is large enough not only to fit over the rubber pad 92 but to leave a perimeter which is caught in the rim of the cup like member 96 when the latter is screwed onto the threaded rod 86 against the mushroom shaped cap 90.

The casing 10 supports a carrying handle generally denoted by the numeral 98 which includes a circular cross bar 100 spaced from the casing 10 and opposed to the rocker plate 70. The cross bar 100 is secured to the corresponding ends of a pair of spaced apart plates 102, each having a pair of apertures adjacent the other end. The hollow rubber bushings 20 provided in the side walls 16 fit into these apertures, and the handle 98 is secured to the rigid inner structure by means of screws 106 extending through the rubber bushings 20, and the pad 22 to terminate in threaded aperture 104 in vertical plates 108 carried by the plate 42.

Although the handle 98 is resiliently insulated from the rigid structure it is not intended to be held by the operator while the massage elements 84 are in contact with the body tissue because the oscillation of the handle 98 renders the hands insensitive.

It is a feature of the invention that the device may be used with practically no vibration being transmitted to the hands of the operator. This is accomplished by a circular abutment 110 on each plate 102, which circular abutments 110 constitutes separate holding means resiliently insulated from the rigid structure of the device by the hollow rubber bushings 20 which in turn insulate the handle 98. The circular abutments 110 are preferably placed above the elastomeric plate member 76 but at the location of minimum motion of the rigid structure when the device is operative.

The device is primarily intended for connection to the standard electrical supply and to facilitate its use therewith the motor 50 is of the synchronous type delivering about 1650 revolutions per minute. If the device is too light the massage elements 84 will bounce too much despite the application of pressure by the operator. On the other hand the device, to be portable and conducive to manipulation by the operator, must not be too heavy. Accordingly the weight of the device is arranged so that the moment of force above the elastomeric pivot 76 is sufficient to cause slowing of the motor when the massage elements 84 act on the body tissue. This is arranged so that with the operator holding the device by the abutments 110 to apply minimum pressure the load causes the massage elements 84 to operate down to about a frequency of about 22 cycles per second. Motor characteristics and supply are variable but, by way of example and not by way of limitation, it has been found that with a four pole synchronous motor operating at about 1650 r.p.m. the weight of the device is between $6\frac{1}{2}$ to $7\frac{1}{2}$ lbs. The frequency of 22 cycles per second is desirable because it appears to have the maximum penetrative effect on the body tissue, otherwise known as deep muscle massage and because of the location of the abutments 110 a stroke of up to 1" of the massage elements 84 can be handled by the operator.

It has also been found that the position of the abutments 110 enables the operator to apply increased pressure which has the effect of lowering the frequency of the massage elements 84. In particular with the device weighted to operate at 22 cycles per second as described above, increasing pressure on the abutments 110 can be exerted to such a degree that the moment of force about the elastomeric pivot 76 will cause slowing of the motor 50 with the result that the massage elements 84 operate on body tissue down to about 12 cycles per second or lower e.g. 6 cycles per second depending on the nature of the body tissue.

It is often desirable to change the amplitude of the massage members instantly during deep muscle massage. This is achieved by including specific weight means, generally denoted by the numeral 112, in the rigid structure which is adjustable in position in relation to the elastomeric pivotal mounting 76 of the rocker plate 70. The weight 112 is located on the platform 44b thus being removed from the flexible coupling 66 with respect to the elastomeric plate member 76.

A particularly convenient form of adjustable weight means 112 is illustrated in FIG. 4 and comprises a circular block 114 rotatably mounted on a spindle 116 extending upwards from the platform 44b. The circular block 14 has an arm 118 projecting normally therefrom to extend outward through the slot 28 in the casing 10. The circular block 114 is eccentrically weighted by including in one position only a portion 120 of a heavier material e.g. the block 114 is made of plastic while the portion 120 is lead.

It will be apparent that movement of the arm 112 in the slot 28 will change the position of the portion 120 in relation to the pivotal mounting of the rocker plate 70 on the transverse bar 78. As the portion 120 is moved inward the amplitude of the massage elements 84 will diminish. When the massage elements 84 are placed against body tissue, the weight of the device is sufficient to provide a stroke of the elements of up to 1" when the device is held in position by the abutments 110. If the stroke is to be changed the position of the weighted portion of the circular block is then changed but otherwise the amplitude will be constant because the pressure is derived from the weight.

The location of minimum motion of the device can be determined by a strobescope. A fan may be mounted on the motor 50 to provide additional cooling of the device when operated for extended periods at the lower frequency of about 12 cycles per second.

I claim:

1. A method of massage treatment of deep muscle in body tissue comprising the steps of attaching to the skin of the person being treated a pair of electrodes of a galvanic skin reactor to complete the circuit, applying to said body tissue reciprocating massage elements intended to to cause muscular stretch reflex to affected muscles, which reflex will change the resistance between said pair of electrodes and the underlying skin and measuring the response of said galvanic skin reactor indicating the change in resistance between said electrodes and the enclosed skin caused by said application of said massage elements to said body tissue.

* * * * *